US00PP34296P2

(12) United States Plant Patent
Wood

(10) Patent No.: US PP34,296 P2
(45) Date of Patent: Jun. 7, 2022

(54) ***PHILADELPHUS* PLANT NAMED 'SMNPVB'**

(50) Latin Name: *Philadelphus hybrida*
Varietal Denomination: SMNPVB

(71) Applicant: Timothy D. Wood, Spring Lake, MI (US)

(72) Inventor: Timothy D. Wood, Spring Lake, MI (US)

(73) Assignee: SPRING MEADOW NURSERY INC., Grand Haven, MI (US)

( * ) Notice: Subject to any disclaimer, the term of this patent is extended or adjusted under 35 U.S.C. 154(b) by 0 days.

(21) Appl. No.: 17/492,631

(22) Filed: Oct. 3, 2021

(51) Int. Cl.
*A01H 5/02* (2018.01)
*A01H 6/48* (2018.01)

(52) U.S. Cl.
USPC ..... Plt./226
CPC ..... *A01H 6/48* (2018.05)

(58) Field of Classification Search
USPC ..... Plt./226
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Philadelphus* plant named 'SMNPVB', characterized by its compact, upright to somewhat outwardly spreading and uniformly mounding plant habit; moderately vigorous growth habit and rapid growth rate; freely branching habit; dense and bushy appearance; green and greenish yellow variegated leaves; numerous fragrant white-colored flowers; and good garden performance.

3 Drawing Sheets

Figure 1:
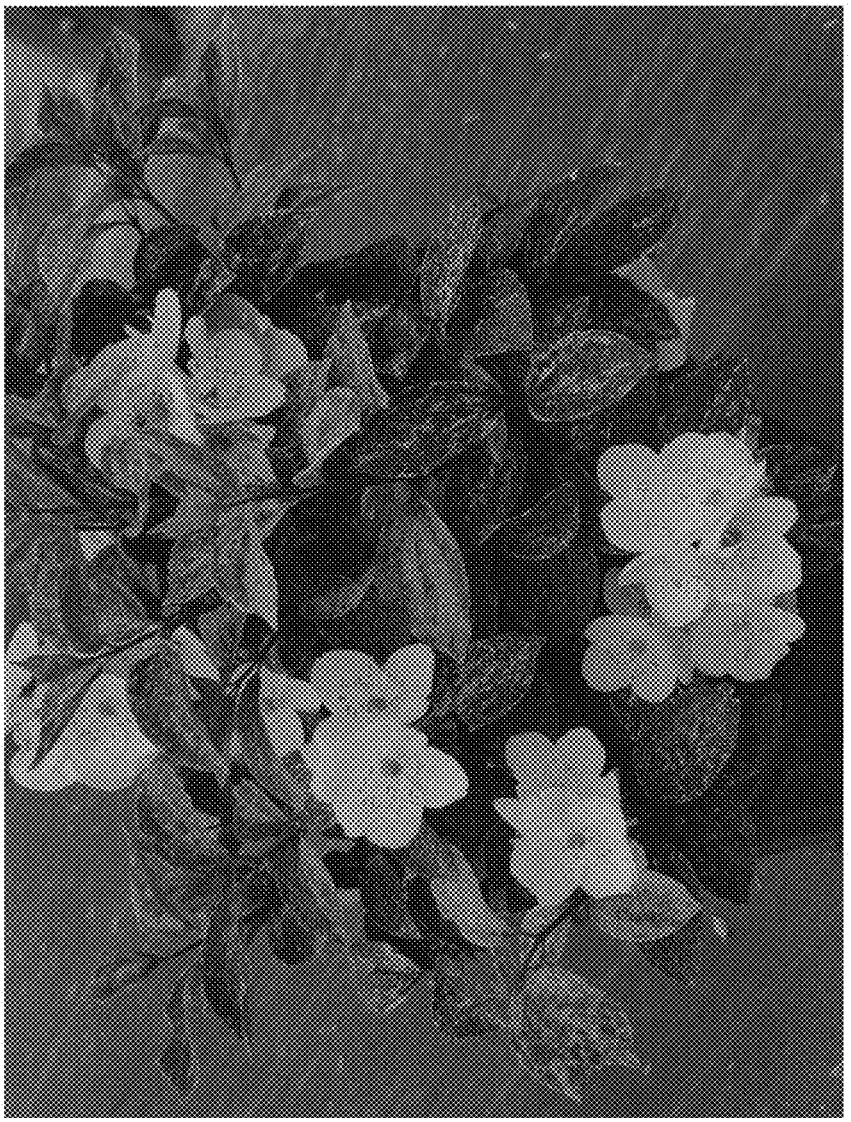

Botanical designation: *Philadelphus hybrida.*
Cultivar denomination: 'SMNPVB'.

STATEMENT REGARDING PRIOR DISCLOSURES BY INVENTOR/APPLICANT & ASSIGNEE

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Philadelphus* plant, botanically known as *Philadelphus hybrida*, commonly referred to as Mock Orange and hereinafter referred to by the cultivar name 'SMNPVB'.

The new *Philadelphus* is a product of a planned breeding program conducted by the Inventor in Grand Haven, Mich. The objective of the breeding program was to develop new compact and freely flowering *Philadelphus* plants with unique leaf coloration.

The new *Philadelphus* plant is a naturally-occurring whole plant mutation of an unnamed proprietary selection of *Philadelphus hybrida*, not patented. The new *Philadelphus* plant was discovered and selected by the Inventor during the spring of 2015 as a single plant from within a population of plants of the mutation selection in a controlled environment in Grand Haven, Mich.

Asexual reproduction of the new *Philadelphus* plant by softwood stem cuttings in a controlled greenhouse environment in Grand Haven, Mich. since 2015 has shown that the unique features of this new *Philadelphus* plant are stable and reproduced true to type in successive generations of asexual reproduction.

SUMMARY OF THE INVENTION

Plants of the new *Philadelphus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNPVB'. These characteristics in combination distinguish 'SMNPVB' as a new and distinct *Philadelphus* plant:

1. Compact, upright to somewhat outwardly spreading and uniformly mounding plant habit.
2. Moderately vigorous growth habit and rapid growth rate.
3. Freely branching habit; dense and bushy appearance.
4. Green and greenish yellow variegated leaves.
5. Numerous fragrant white-colored flowers.
6. Good garden performance.

Plants of the new *Philadelphus* can be compared to plants of the mutation parent selection. In side-by-side comparisons, plants of the new *Philadelphus* have variegated leaves whereas plants of the mutation parent selection have non-variegated leaves.

Plants of the new *Philadelphus* can also be compared to plants of *Philadelphus lemoinei* 'Innocence', not patented.

In side-by-side comparisons, plants of the new *Philadelphus* differ primarily from plants of 'Innocence' in the following characteristics:

1. Plants of the new *Philadelphus* are more compact than plants of 'Innocence'.
2. Plants of the new *Philadelphus* are more freely branching and denser than plants of 'Innocence'.
3. Developing leaves of plants of the new *Philadelphus* are more highly variegated than developing leaves of plants of 'Innocence'.
4. Plants of the new *Philadelphus* are less susceptible to sun scalding than plants of 'Innocence'.

BRIEF DESCRIPTION OF THE PHOTOGRAPHS

The accompanying colored photographs illustrate the overall appearance of the new *Philadelphus* plant showing the colors as true as it is reasonably possible to obtain in colored reproductions of this type. Colors in the photographs may differ slightly from the color values cited in the detailed botanical description which accurately describe the colors of the new *Philadelphus* plant.

The photograph on the first sheet (FIG. 1) is a side perspective view of a typical flowering plant of 'SMNPVB'.

Figure 2:
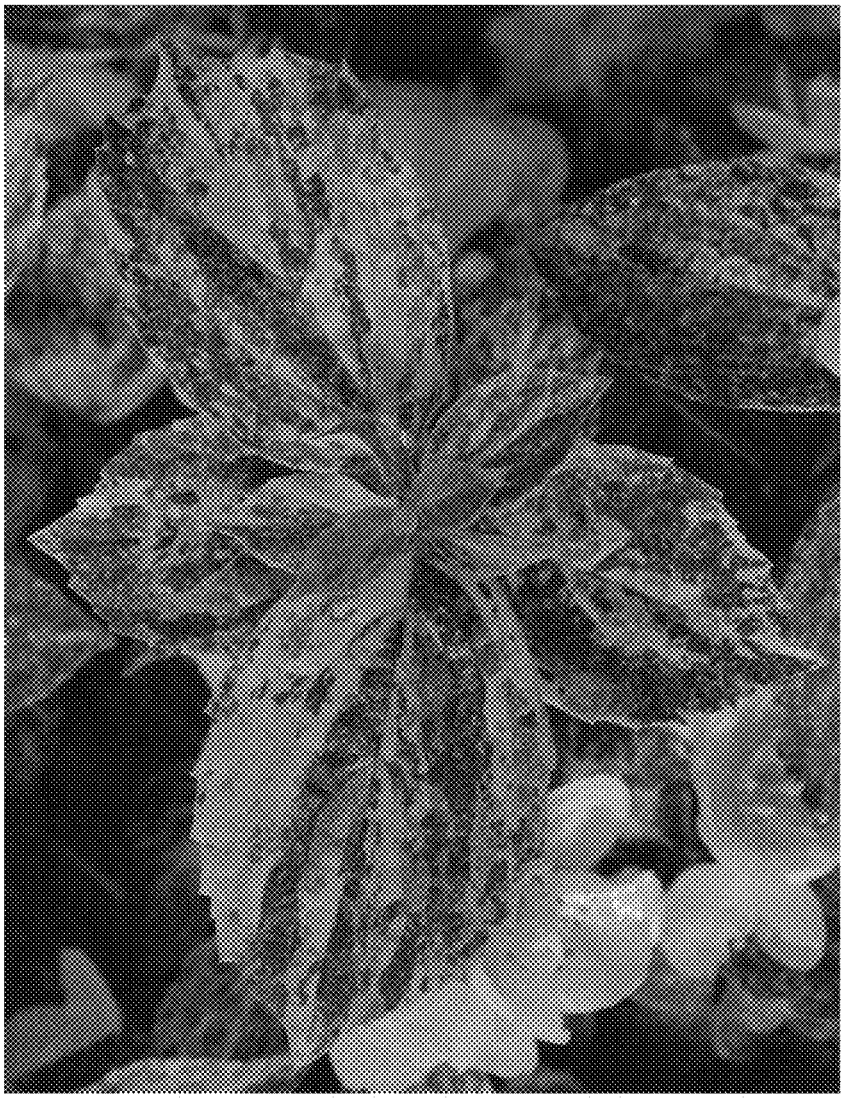

The photograph on the second sheet (FIG. 2) is close-up view of typical leaves of 'SMNPVB'.

Figure 3:
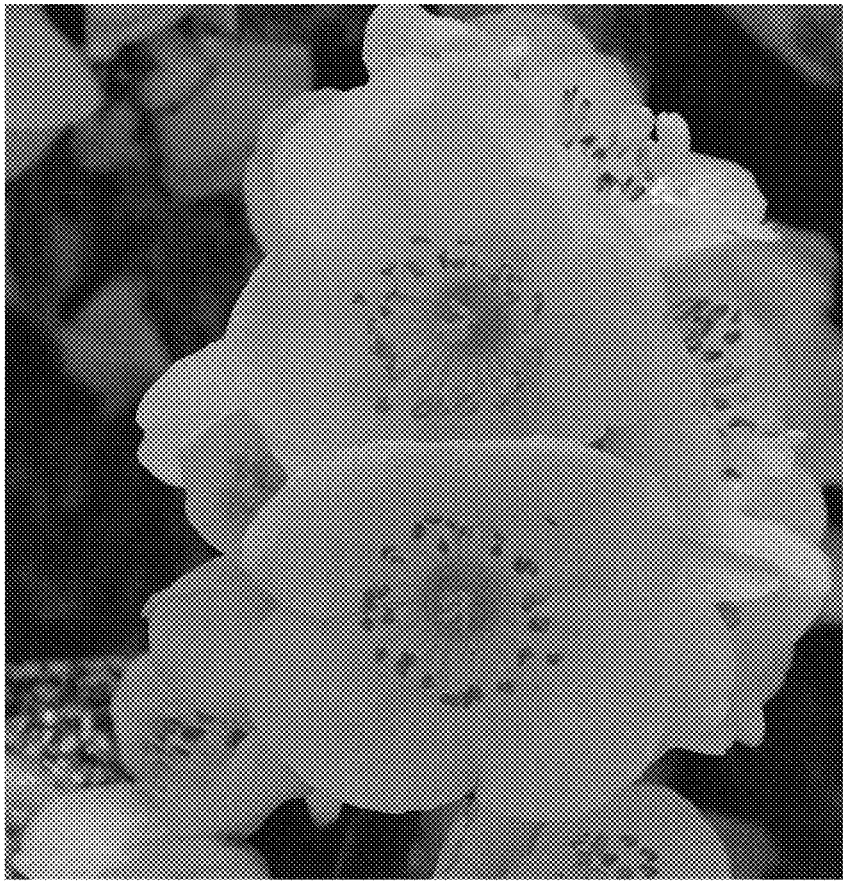

The photograph on the third sheet (FIG. 3) is a close-up view of typical flowers of 'SMNPVB'.

DETAILED BOTANICAL DESCRIPTION

The aforementioned photographs and following observations, measurements and values describe plants grown in the spring in three-gallon containers in a polypropylene-covered shadehouse in Grand Haven, Mich. and under cultural practices typical of commercial *Philadelphus* production. During the production of the plants, day temperatures ranged from 18° C. to 27° C. and night temperatures ranged from 5° C. to 10° C. Plants were three years old when the photographs and the description were taken. In the description, color references are made to The Royal Horticultural Society Colour Chart, 2015 Edition, except where general terms of ordinary dictionary significance are used.

Botanical classification: *Philadelphus hybrida* 'SMNPVB'.

Parentage: Naturally-occurring whole plant mutation of an unnamed proprietary selection of *Philadelphus hybrida*, not patented.

Propagation:

- *Type*.—By softwood stem cuttings.
- *Time to initiate roots, summer*.—About two weeks at temperatures about 18° C. to 27° C.
- *Time to produce a rooted young plant, summer*.—About two months at temperatures about 18° C. to 27° C.
- *Root description*.—Thick to fine; fibrous; typically white to brown in color, actual color of the roots is dependent on substrate composition, water quality, fertilizer, substrate temperature and physiological age of roots.
- *Rooting habit*.—Freely branching; dense.

Plant description:

- *Plant form and growth habit*.—Perennial deciduous shrub; compact, upright to somewhat outwardly spreading and uniformly mounding plant habit; moderately vigorous growth habit and rapid growth rate.
- *Branching habit*.—Freely branching habit; more than ten lateral branches develop per plant; pinching enhances lateral branch development.
- *Plant height*.—About 40 cm.
- *Plant diameter* (*area of spread*).—About 35 cm.

Lateral branch description:

- *Length*.—About 35 cm.
- *Diameter*.—About 7 mm.
- *Internode length*.—About 3 cm.
- *Aspect*.—Erect to about 20° from vertical.
- *Strength*.—Strong.
- *Texture*.—When developing, slightly pubescent; with development becoming smooth and glabrous and when woody, rough.
- *Color, developing, upper and lower surfaces*.—Close to 144B.
- *Color, developed, lower surface*.—Close to N199C.

Leaf description:

- *Arrangement*.—Opposite, simple.
- *Length*.—About 5.5 cm.
- *Width*.—About 3.5 cm.
- *Shape*.—Elliptic.
- *Apex*.—Acute to acuminate.
- *Base*.—Cuneate.
- *Margin*.—Serrulate.
- *Texture, upper surface*.—Somewhat coarse; glabrous.
- *Texture, lower surface*.—Somewhat coarse with pronounced venation; mostly glabrous with pubescence along venation.
- *Venation pattern*.—Pinnate.
- *Color*.—Developing leaves, upper surface: Variegated with random sectors and splotches, close to 137A and 153D. Developing leaves, lower surface: Close to 147B with variegation pattern of upper surface is visible. Fully expanded leaves, upper surface: Variegated with random sectors and splotches, close to 137A and 4C; venation, close to 144B. Fully expanded leaves, lower surface: Close to 147B with variegation pattern of upper surface is visible; venation, close to 144B.
- *Petioles*.—Length: About 1 cm. Diameter: About 1.5 mm. Texture, upper and lower surfaces: Slightly pubescent. Color, upper and lower surfaces: Close to 144B.

Flower description:

- *Flower appearance and arrangement*.—Rotate flowers arranged in terminal cymes; freely flowering habit with about three to nine flowers developing per inflorescence with more than 200 flowers developing per plant during the flowering season; flowers face mostly upright.
- *Fragrance*.—Slightly fragrant; sweet and pleasant, citrus-like.
- *Natural flowering season*.—Plants flower continuously during the spring in Michigan; flowers not persistent.
- *Inflorescence height*.—About 4 cm.
- *Inflorescence diameter*.—About 5 cm.
- *Flower diameter*.—About 4 cm by 4 cm.
- *Flower depth*.—About 1 cm.
- *Flower buds*.—Length: About 8 mm. Diameter: About 8 mm. Shape: Ovoid. Color: Close to 144B and N144D.
- *Petals*.—Quantity and arrangement: Four or five arranged in a single whorl. Length: About 2 cm. Width: About 1.5 cm. Shape: Elliptic. Apex: Obtuse.

Base: Truncate. Margin: Entire. Texture, upper and lower surfaces: Smooth; soft and delicate; glabrous. Color: When opening, upper and lower surfaces: Close to NN155B; median streaks, close to 157B. Fully opened, upper and lower surfaces: Close to NN155B; median streaks, close to 157B.

*Petaloids*.—Quantity and arrangement: About 4 to 20 arranged in one to several whorls. Length: About 1.5 cm to 2 cm. Width: About 5 mm to 10 mm. Shape: Irregular, roughly narrowly elliptic. Apex: Obtuse. Base: Attenuate. Margin: Entire. Texture, upper and lower surfaces: Smooth; soft and delicate; glabrous. Color: When opening and fully opened, upper surface: Close to NN155B; towards the apex, close to 157B. When opening and fully opened, lower surface: Close to NN155B.

*Sepals*.—Quantity and arrangement: Four to five in a single whorl. Length: About 6 mm. Width: About 4 mm. Shape: Teardrop-shaped. Apex: Acuminate. Base: Truncate. Margin: Entire. Texture, upper and lower surfaces: Slightly pubescent. Color, upper and lower surfaces: Close to 144B and N144D.

*Peduncles*.—Length: About 2 cm. Diameter: About 2 mm. Aspect: Mostly erect. Strength: Strong. Texture: Smooth, glabrous. Color, upper and lower surfaces: Close to 144B.

*Pedicels*.—Length: About 1 cm. Diameter: About 1 mm. Aspect: About 30° to 45° from peduncle axis. Strength: Strong; flexible. Texture: Smooth, glabrous. Color, upper and lower surfaces: Close to 144B.

*Reproductive organs*.—Stamens: Quantity per flower: About 30; dithecal; basifixed. Filament length: About 1 cm. Filament color: Close to NN155B. Anther length: About 1.5 mm. Anther shape: Rounded. Anther color: Close to 12B. Pollen amount: Scarce. Pollen color: Close to 12B. Pistils: Quantity per flower: Four. Pistil length: About 7 mm. Stigma shape: Oblong. Stigma color: Close to 157A. Style length: About 6 mm. Style color: Close to 157A. Ovary color: Close to 145C.

*Fruits and seeds*.—To date, fruit and seed development have not been observed on plants of the new *Philadelphus*.

Garden performance: Plants of the new *Philadelphus* have been observed to have good garden performance.

Pathogen & pest resistance: To date, plants of the new *Philadelphus* have not been shown to be resistant to pathogens and pests common to *Philadelphus* plants.

It is claimed:

1. A new and distinct *Philadelphus* plant named 'SMNPVB' as illustrated and described.

* * * * *